United States Patent
Arima

(10) Patent No.: US 12,384,645 B2
(45) Date of Patent: Aug. 12, 2025

(54) METHOD AND DEVICE FOR MANUFACTURING WEARABLE ARTICLE

(71) Applicant: ZUIKO CORPORATION, Osaka (JP)

(72) Inventor: Takashi Arima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 59 days.

(21) Appl. No.: 18/289,952

(22) PCT Filed: Jun. 29, 2022

(86) PCT No.: PCT/JP2022/025921
§ 371 (c)(1),
(2) Date: Nov. 8, 2023

(87) PCT Pub. No.: WO2023/002819
PCT Pub. Date: Jan. 26, 2023

(65) Prior Publication Data
US 2024/0262648 A1 Aug. 8, 2024

(30) Foreign Application Priority Data
Jul. 22, 2021 (JP) .................................. 2021-121089

(51) Int. Cl.
*B65H 35/04* (2006.01)
*A61F 13/15* (2006.01)
(Continued)

(52) U.S. Cl.
CPC ....... *B65H 35/04* (2013.01); *A61F 13/15723* (2013.01); *A61F 13/15764* (2013.01);
(Continued)

(58) Field of Classification Search
None
See application file for complete search history.

(56) References Cited

U.S. PATENT DOCUMENTS

2004/0089403 A1    5/2004  Satoh
2008/0236756 A1   10/2008  Nakakado
(Continued)

FOREIGN PATENT DOCUMENTS

EP    3064178 A1    9/2016
JP    2004-148040 A    5/2004
(Continued)

OTHER PUBLICATIONS

International Search Report for corresponding Application No. PCT/JP2022/025921, mailed Sep. 13, 2022.

*Primary Examiner* — Barbara J Musser
(74) *Attorney, Agent, or Firm* — Renner, Otto, Boisselle & Sklar, LLP

(57) ABSTRACT

A manufacturing method for a wearing item repeatedly executes: a step of, at a preceding pad, receiving and holding a distal end part of a continuous body to convey; a step of, at a following pad, catching up with the preceding pad; a both holding step of, at both of the preceding pad and the following pad, holding the continuous body; and a cutting step of cutting the distal end part of the continuous body to generate an individual workpiece on the preceding pad, and, in the both holding step, relative speeds of both of the pads are equal to each other, and both of the pads rotate at a non constant speed in at least part of a zone, the continuous body is fed from the feeder at the non-constant speed in response to a change in a speed of the pads that rotate at the non-constant speed.

7 Claims, 8 Drawing Sheets

(51) Int. Cl.
  *B65H 5/12* (2006.01)
  *B65H 20/34* (2006.01)
  *B65H 39/14* (2006.01)

(52) U.S. Cl.
  CPC ......... *A61F 13/15804* (2013.01); *B65H 5/12* (2013.01); *B65H 20/34* (2013.01); *B65H 39/14* (2013.01)

(56) References Cited

U.S. PATENT DOCUMENTS

| | | |
|---|---|---|
| 2008/0289468 A1 | 11/2008 | Nakakado et al. |
| 2015/0223992 A1 | 8/2015 | Maehara et al. |

FOREIGN PATENT DOCUMENTS

| | | |
|---|---|---|
| JP | 2015-84906 A | 5/2015 |
| WO | 2005/005296 A1 | 1/2005 |
| WO | 2005/075163 A1 | 8/2005 |
| WO | 2005/085108 A1 | 9/2005 |

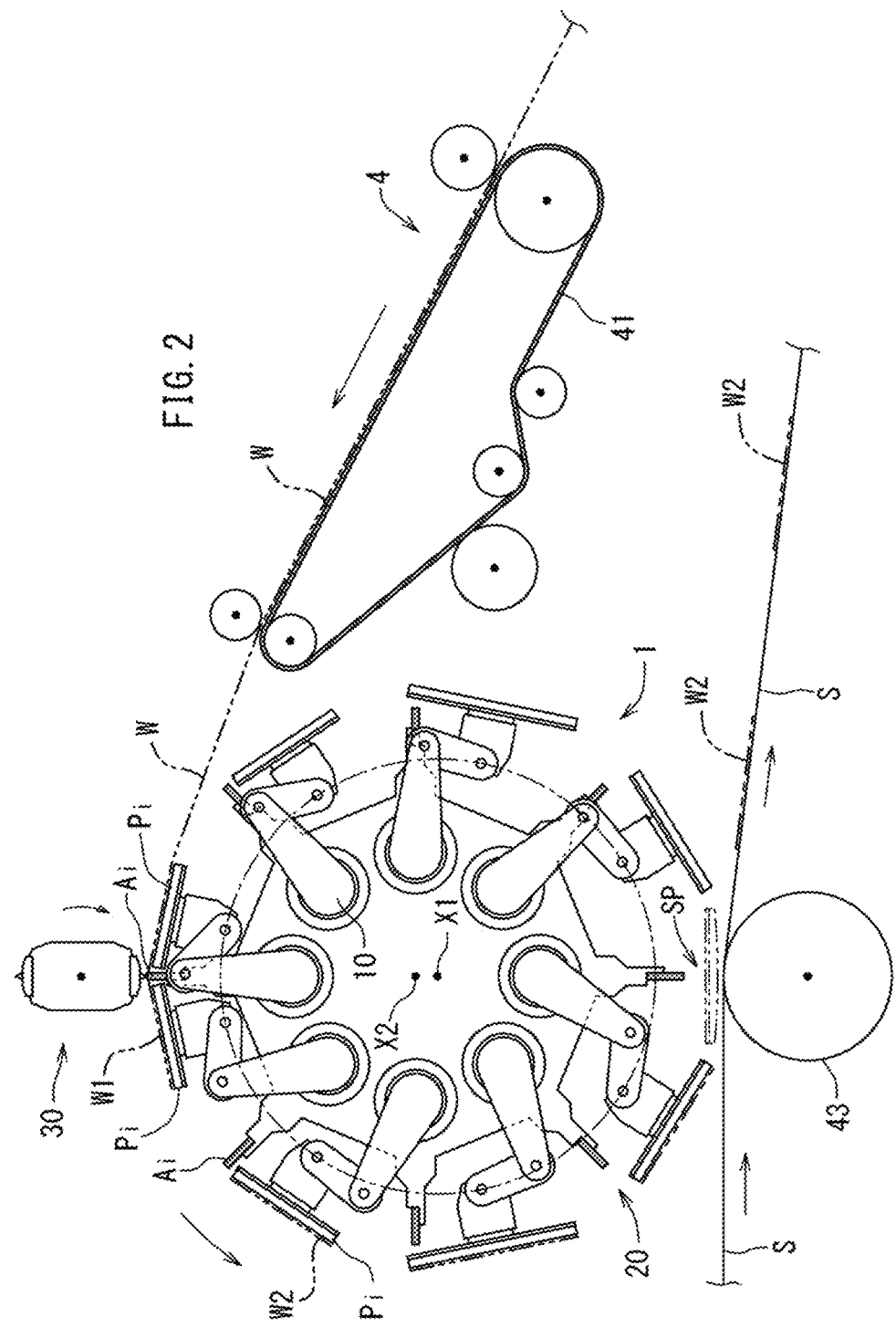

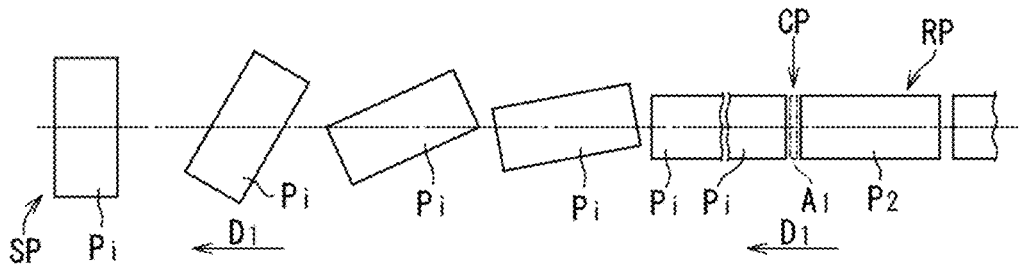
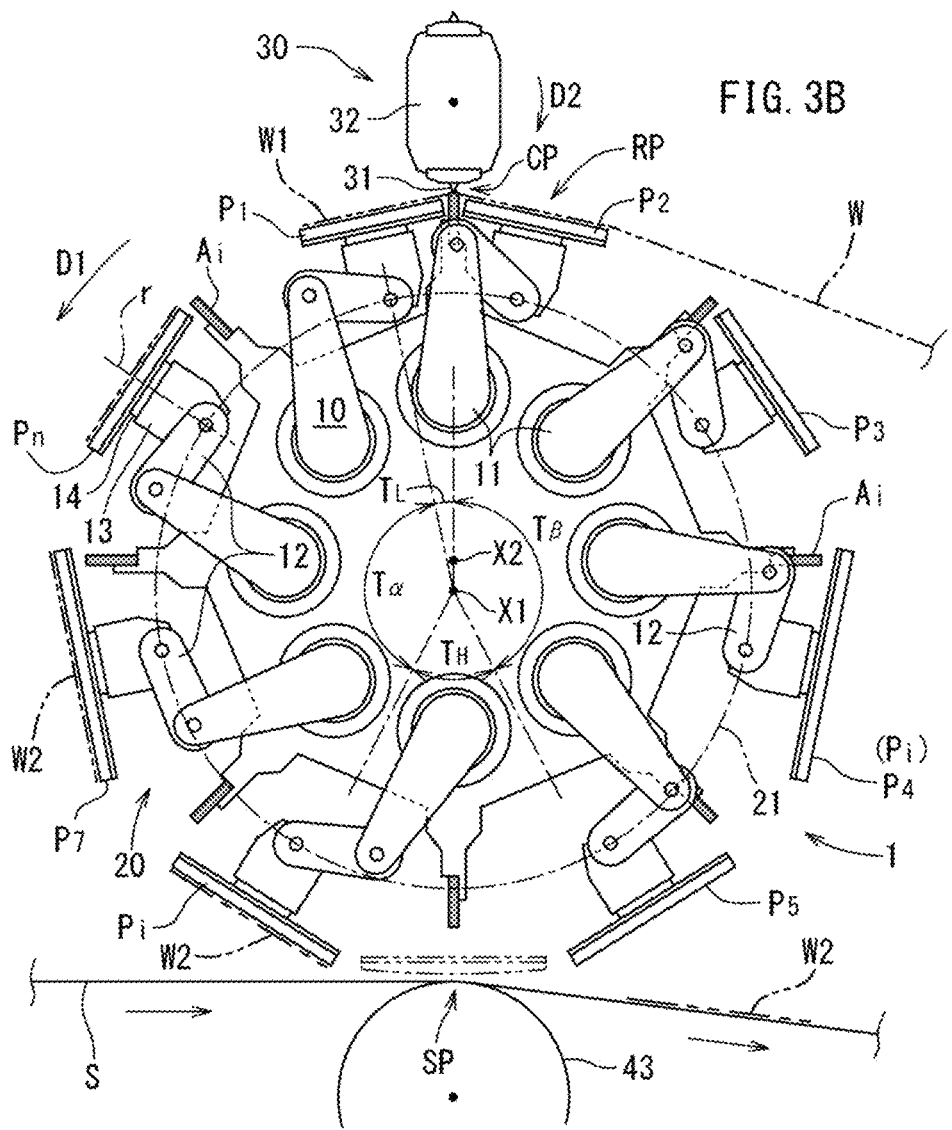

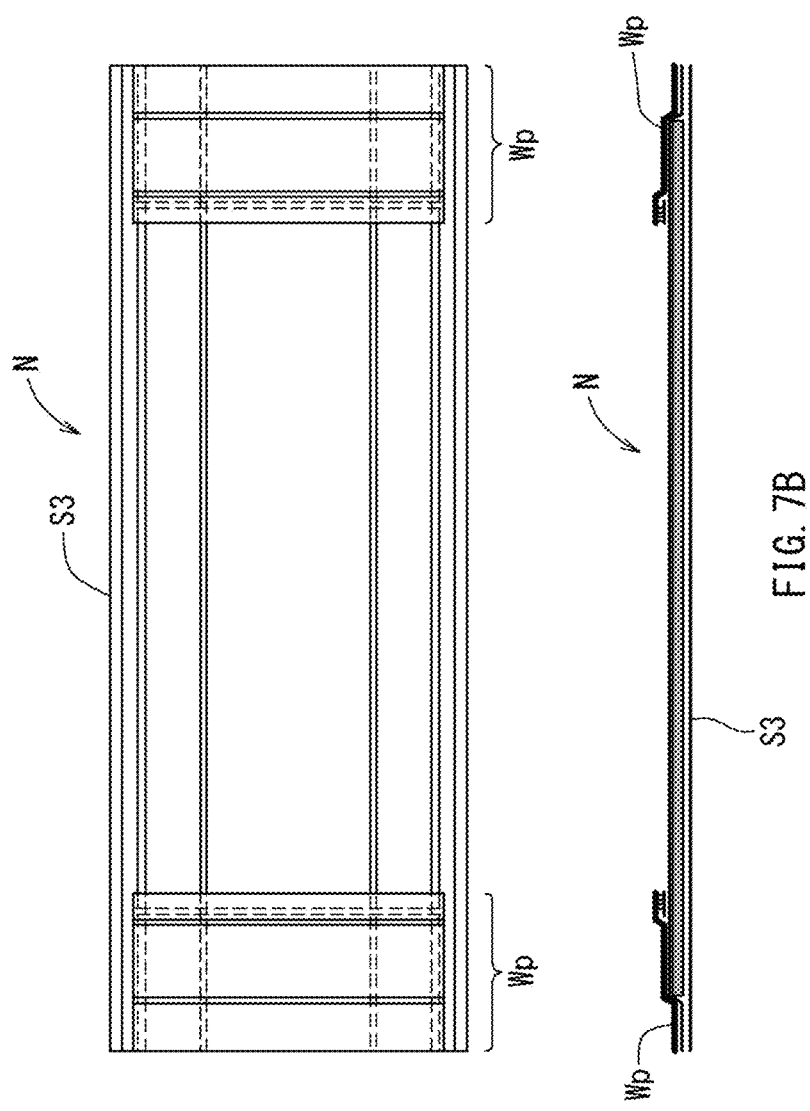

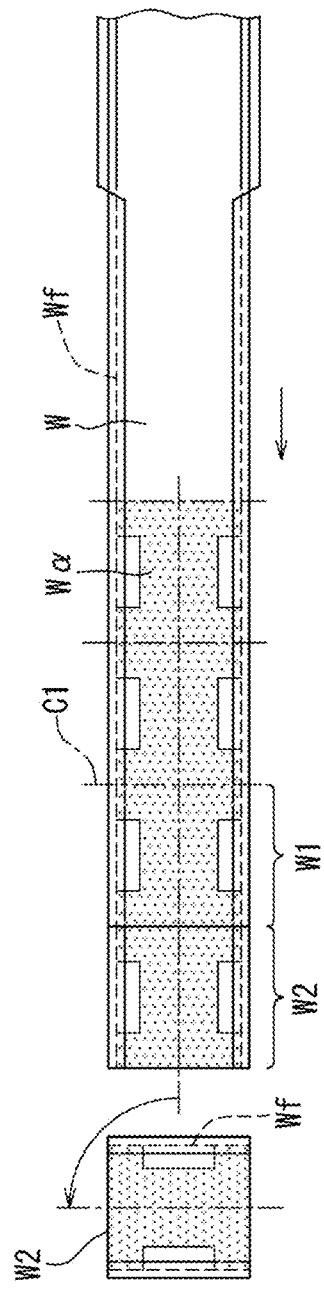
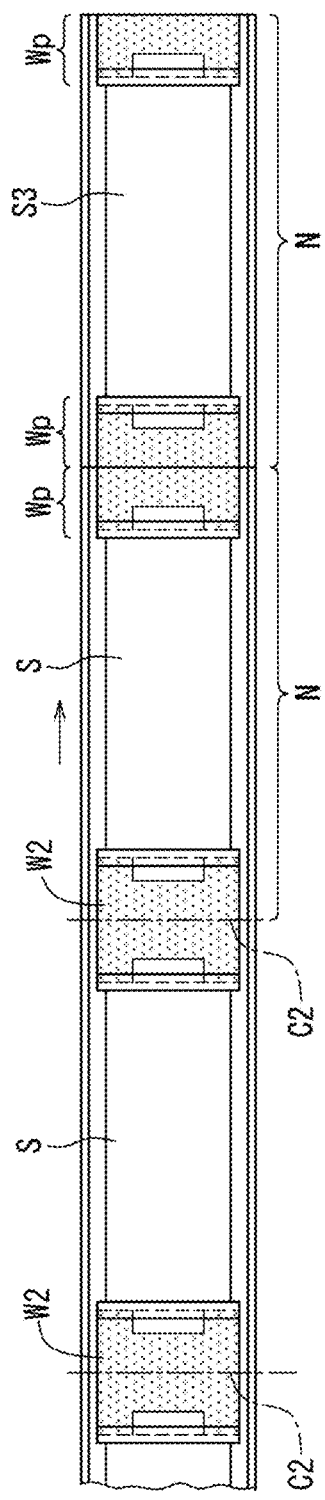

METHOD AND DEVICE FOR MANUFACTURING WEARABLE ARTICLE

TECHNICAL FIELD

The present invention relates to a manufacturing method and a manufacturing device for a wearing item.

BACKGROUND ART

A manufacturing method and device for wearing items that expand a distance between neighboring workpieces and arrange the workpieces on a continuous sheet are known (Patent Literature 1).

According to an invention of following Patent Literature 1, a rotary drum including a plurality of pads receives a workpiece continuous body, the workpiece continuous body is cut into individual workpieces between the neighboring pads, a rotation speed of the pads is changed while the pads that hold the individual workpieces rotate to change a distance between the neighboring pads (workpieces), and then the workpieces are arranged on a continuous sheet that is conveyed at a predetermined speed.

CITATION LIST

Patent Literature

Patent Literature 1: WO 2005/075163 A

SUMMARY OF INVENTION

It is desirable to adjust a feeding speed of a workpiece continuous body to the rotation speed of pads when the workpiece continuous body is fed to the pads.

Conventionally, at the time of the above feeding, the feeding speed of the workpiece continuous body is a constant speed, and therefore the pads also need to rotate at the constant speed at the time of reception. However, in a case where a zone in which the rotation speed of the pads is the constant speed is long, an acceleration zone of pads becomes short, and therefore problems occur that a distance between the neighboring pads, that is, between the workpieces cannot be sufficiently increased, and the diameter of the rotary drum becomes large.

It is therefore an object of the present invention to provide a manufacturing method and a manufacturing device for a wearing item that can change pitches between neighboring workpieces to large pitches without making the diameter of a rotary drum larger.

Note that the wearing item according to the present invention includes items such as disposable wearing items and absorptive items that are part of the disposable wearing items.

A manufacturing method according to the present invention is a manufacturing method for a wearing item for feeding a continuous body from a feeder to a drum including a plurality of pads that rotate with a circumferential speed being changed, cutting a distal end part of the continuous body one after another to generate individual workpieces on the pads one after another, and passing the workpieces to a downstream process in a state where a distance between the pads that hold the workpieces is expanded, and an interval between neighboring workpieces is increased, the method repeatedly executes: a step of, at a preceding pad, receiving and holding the distal end part of the continuous body to convey; a step of, at a following pad, catching up with the preceding pad; a both holding step of, at both of the preceding pad and the following pad, holding the continuous body; and a cutting step of cutting the distal end part of the continuous body to generate the individual workpiece on the preceding pad, and in the both holding step, relative speeds of both of the pads are equal to each other, and both of the pads rotate at a non-constant speed in at least part of a zone, and the continuous body is fed from the feeder at the non-constant speed in response to a change in a speed of the pads that rotate at the non-constant speed.

Meanwhile, a manufacturing device according to the present invention is a manufacturing device for a wearing item that feeds a continuous body to a drum including a plurality of pads that rotate with a circumferential speed being changed, cuts a distal end part of the continuous body one after another to generate individual workpieces on the pads one after another, and passes the workpieces to a downstream process in a state where a distance between the pads that hold the workpieces is expanded, and an interval between neighboring workpieces is increased, and includes: a preceding pad that receives and holds the distal end part of the continuous body to convey; a following pad that catches up with the preceding pad and holds the continuous body together with the preceding pad; a cutter that cuts the distal end part of the continuous body to generate the individual workpiece on the preceding pad; a workpiece speed changer device that controls rotation of each pad in a state where both of the preceding pad and the following pad hold the continuous body such that relative speeds of both of the pads are equal to each other, and both of the pads rotate at a non-constant speed in at least part of a zone; and a feeder that feeds the continuous body to the drum at the non-constant speed in response to a change in a speed of the pads that rotate at the non-constant speed.

According to the present invention, in the both holding step where both of the preceding and following pads hold the continuous body, the relative speeds of both of the pads are equal to each other, so that there is no concern that an unintended tension is produced at a portion of the continuous body between both of the pads. Meanwhile, both of the pads rotate at the non-constant speed in at least part of the zone in the both holding step, and the continuous body is fed from the feeder at the non constant speed in response to this change in the speed of the pads, so that it is possible to change the speeds of the pads from a point of time when the continuous body starts being fed. Consequently, it is possible to shorten the zone of the constant speed, and increase the pitches between the neighboring workpieces without increasing the diameter of the drum.

BRIEF DESCRIPTION OF DRAWINGS

FIG. 2 is a schematic front view illustrating a workpiece conveying device including a drum, and a feeder.

FIG. 3A is a development view illustrating a change in postures of pads that hold cut webs, and FIG. 3B is a schematic front view illustrating the drum and the like.

FIG. 7A is a plan view illustrating an example of an individual wearing item (absorptive item), FIG. 7B is a front view of the individual wearing item, and FIG. 7C is a side view of the individual wearing item.

FIG. 8 is a schematic front view illustrating an example of a manufacturing process for a wearing item.

DESCRIPTION OF EMBODIMENTS

Figure 1:
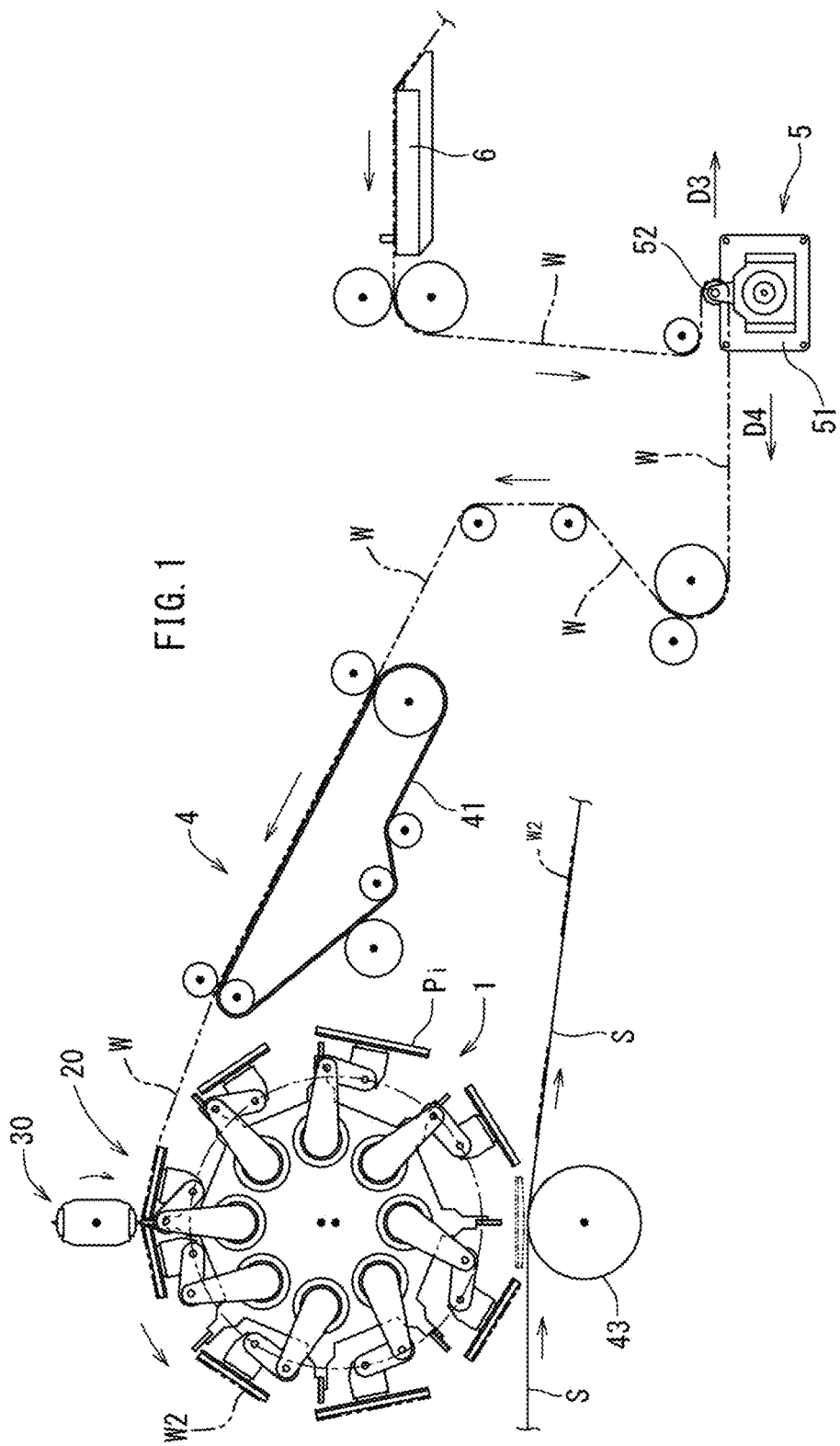
FIG. 1 is a schematic layout view illustrating an embodiment of a manufacturing device for a wearing item according to the present invention.

The present invention will be understood more clearly from the following description of preferred embodiments taken in conjunction with the accompanying drawings. Note however that the embodiment and the drawings are merely illustrative and should not be taken to define the scope of the present invention. The scope of the present invention shall be defined only by the appended claims. In the accompanying drawings, like reference numerals denote like components throughout the plurality of figures.

Hereinafter, the embodiment of the present invention will be described with reference to the drawings. FIGS. 1 to 8 illustrate one embodiment.

FIG. 3B is a schematic front view of a drum and the like according to the embodiment of the present invention.

As illustrated in FIG. 3B, a manufacturing device receives a distal end part W1 of a continuing continuous web W at a reception position RP, and cuts the continuous web W at a cutting position CP at a downstream of the reception position RP. Furthermore, the workpiece conveying device 1 conveys a cut web W2 (an example of a workpiece) in FIG. 3B to an arrangement station SP at the downstream while changing the posture of the cut web W2 formed by cutting the continuous web W by changing the posture of a pad Pi illustrated in FIG. 3A. Subsequently, the workpiece conveying device 1 passes the cut webs W2 onto a continuous absorption body in FIG. 3B one after another at the arrangement station SP.

Note that, to indicate one of pads P1 to Pn in FIG. 3B in the following description, the one pad will be described as a pad Pi.

As illustrated in FIG. 3B, a manufacturing device includes the plurality of pads Pi, a plurality of anvils (edge bases) Ai, and a cutter 30. Note that the anvils Ai are colored gray in each figure to make it easy to see each figure.

The cutter 30 includes, for example, at least one edge 31 fixed to a cutter roll 32. A plurality of the edges 31 may be provided to the cutter 30.

Each anvil Ai receives the edge 31, and may be attached to surroundings of a drum 20. The plurality of anvils Ai may be arranged at equal angle pitches around the drum 20.

The drum 20 rotates in a first direction D1 that is a convey direction of the webs W and W2. Meanwhile, the cutter 30 rotates in a second direction D2 opposite to the first direction D1 in synchronization with the drum 20. That is, the drum 20 and the cutter roll 32 rotate such that, when each anvil Ai reaches the cutting position CP, the edge 31 comes into contact with the anvil Ai. Every time the cutter roll 32 rotates at a predetermined angle (e.g., 180°, i.e., half rotation), the edge 31 comes into contact with the anvil Ai at the cutting position CP, cuts the distal end part W1 of the continuous web W one after another to generate the cut webs W2.

The pads Pi and the anvils Ai in FIG. 3B are alternately arranged around the drum 20, and rotate together with the drum 20 along a circumferential direction of the drum 20.

For example, the pads Pi in FIG. 4 rotate about a first axial line X1 to be described later as a substantial center and in the first direction D1. Meanwhile, the anvils Ai rotate about a second axial line X2 parallel to the first axial line X1 and displaced from the first axial line X1 as a substantial center and in the first direction D1. The second axial line X2 may be, for example, the rotation center of the drum 20.

Figure 4:
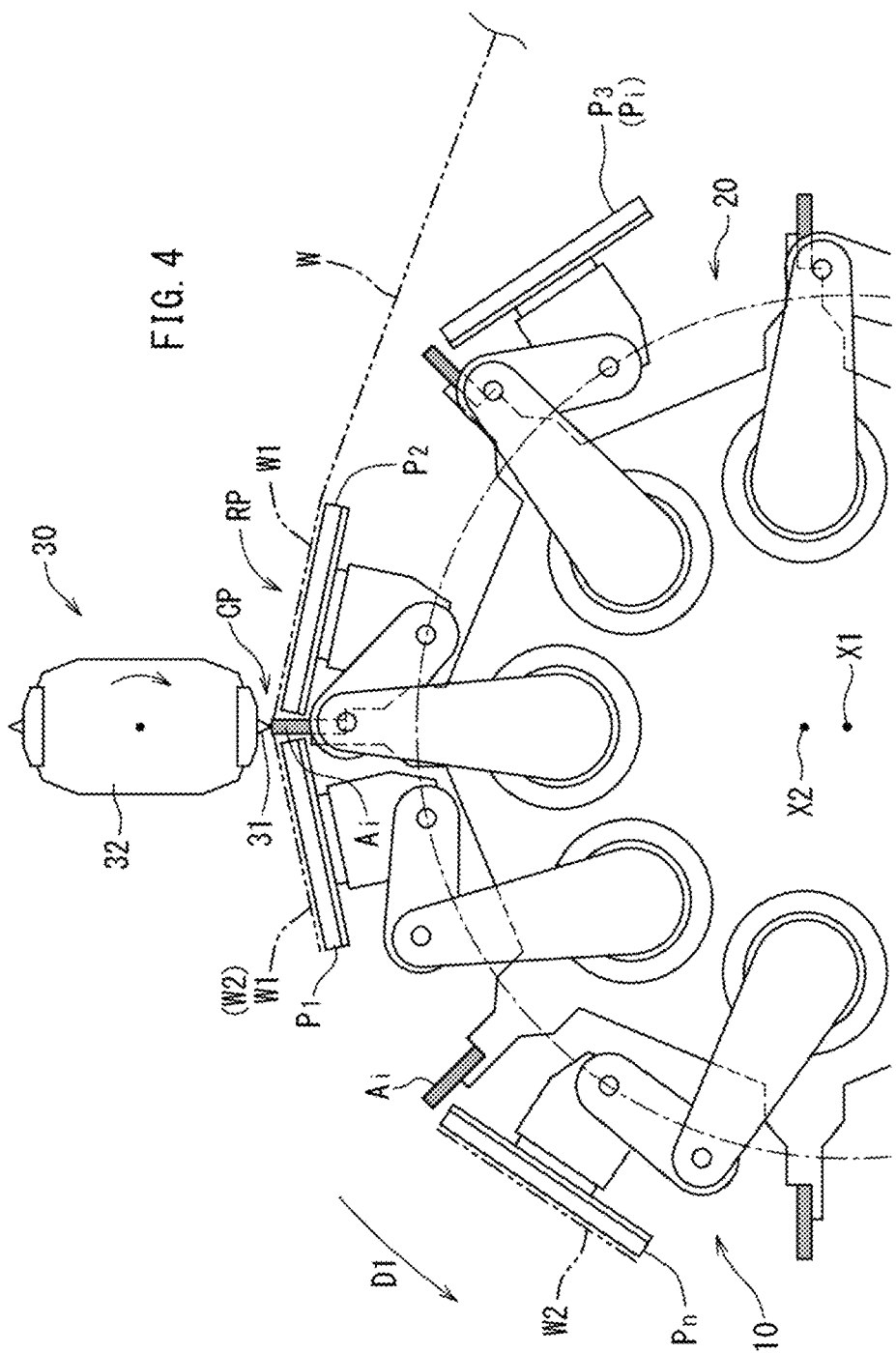
FIG. 4 is a schematic front view illustrating part of the drum in a cutting process.

In FIG. 4, each pad Pi may suction and hold the distal end part W1 of the continuous web W or the cut web W2 on the surface of each pad Pi, or may hook the web W using a needle provided on the surface of each pad Pi to hold. In a case of, for example, a structure that suctions the webs W, W1, and W2 by vacuuming, a plurality of unillustrated suction holes may be opened in the surface of each pad Pi.

In FIG. 3B, after receiving the distal end part W1 of the continuous web W at the reception position RP, each pad Pi rotates in the first direction D1 from the reception position RP. After reception of this distal end part W1, the anvil Ai and the cutter 30 work together to cut the distal end part W1 of the continuous web W at the cutting position CP to generate the cut web W2. After cutting, the cut web W2 on the pad Pi is conveyed to the arrangement station SP. At the arrangement station SP, air may be blown from the suction holes of the pad Pi to make it easy to separate the cut web W2 from the pad Pi.

In FIG. 3B, a plurality of first arms 11 are radially fixed to the drum 20. At the distal end part of each first arm 11, a second arm 12 is rotatably provided to the first arm 11. A pad frame 13 is attached to the distal end of the second arm 12. When the drum 20 rotates, the first and second arms 11 and 12 follow rotation of the drum 20, and the pad frames 13 rotate in the first direction D1 together with the drum 20.

Guiding means 21 that regulates a circular trajectory of the pads Pi is provided at a position indicated by a dashed-dotted line around the drum 20 in FIG. 3B. The guiding means 21 guides the pad frames 13 along a circle whose center is the first axial line X1. Hence, when the pad frame 13 is rotated with the arms 11 and 12 interposed therebetween following rotation of the drum 20, the pad frame 13 rotates about the first axial line X1 while being guided by the guiding means 21. Hence, the pads Pi that rotate about the first axial line X1 and the anvils Ai that rotate about the second axial line X2 make circular motions along mutually different trajectories.

The rotation radius of the pad Pi in FIG. 3B is larger than the rotation radius of each anvil Ai. Furthermore, the first axial line X1 that is the rotation center of the pads Pi is arranged eccentrically toward the arrangement station SP compared to the second axial line X2 that is the rotation center of the anvils Ai. Hence, a relative level of the pads Pi with respect to the anvils Ai is displaced toward an outer side of the drum 20 until the pads Pi reach the arrangement station SP from the cutting position CP. Meanwhile, a relative level of the pads Pi with respect to the anvils Ai is displaced toward an inner side of the drum 20 until the pads Pi reach the vicinity of the cutting position CP from the arrangement station SP.

Note that relative displacement in a radial direction of the pads Pi with respect to the anvils Ai may be performed by moving the pads Pi in the radial direction of the drum 20 by, for example, an air cylinder or a motor in addition to the guiding means 21.

Each pad Pi is rotatably fitted to each pad frame 13 with a turning part 14 interposed therebetween. Each pad Pi is turnable about a normal line r substantially perpendicular to the surface of each pad Pi (the normal line r substantially along a radiation direction of the first axial line X1 (the radial direction of the circular trajectory along which each pad rotates)), that is, a line substantially along the radial direction of the drum 20. Consequently, it is possible to change the posture of the cut web W2. Note that the planar shape of each pad Pi in FIG. 3A is illustrated as a rectangular shape to make it easy to understand a state where the pads Pi are turned, yet may have a shape close to a square shape.

FIG. 3A is a schematic developed view illustrating a turning operation of the pads Pi from the reception position RP to the arrangement station SP.

As illustrated in FIG. 3A, the pad Pi passes the cutting position CP, then starts turning to start changing the posture after the anvil Ai is relatively displaced inward, and is turned at a predetermined angle (e.g., 90°) until the pad Pi reaches the arrangement station SP. Hence, the cut web W2 on the pad Pi is passed to a continuous absorption body S at the downstream in a state where the cut web W2 is turned at the predetermined angle (posture). Note that, until reaching (returning to) the reception position RP from the arrangement station SP in FIG. 3B, the pad Pi is rotated at the predetermined angle (e.g., 90°) and takes such a posture that the pad can receive the continuous web W.

Each pad Pi does not turn at the reception position RP, the cutting position CP, and the arrangement station SP, that is, continues rotating about the first axial line X1 while keeping the same posture.

The above described workpiece conveying device 1 includes a workpiece speed changer device 10. This workpiece speed changer device 10 increases to a transfer speed a convey speed of each cut web W2 conveyed toward the arrangement station SP. A speed change mechanism of this workpiece speed changer device 10 is known, and is executed by motions of the above-described first and second arms 11 and 12.

Note that other structures of the workpiece conveying device 1 is described in WO 2005/075163 A, the entire contents of which are incorporated herein.

Next, an example of a wearing item N will be described with reference to FIGS. 7A to 8B. In FIGS. 7A to 7C, the wearing item N according to the present invention may be an absorptive item formed by bonding a pair of pocket members Wp to both end parts in a longitudinal direction of an absorptive main body S3. This absorptive item may be manufactured as follows.

Both side edges along the longitudinal direction of the continuous web W illustrated in FIG. 8A are folded, and elastic members such as rubber threads Wf are arranged at these both side edges to be folded. A bonding area Wα of this continuous web W indicated by a dot pattern may be applied an adhesive. The distal end part W1 is cut from the continuous web W along a virtual first cutting line C1 to generate the cut web W2, and this cut web W2 is intermittently arranged on the continuous absorption body S at pitches corresponding to a unit of the one wearing item N.

In a case of this example, this continuous absorption body S is cut along a virtual second cutting line C2 that divides the cut web W2 into two at positions that are both ends in the longitudinal direction of the wearing item N to generate the individual wearing items N. That is, the one cut web W2 is a pair of the pocket members Wp of the neighboring wearing items N. Therefore, it is necessary to arrange the respective cut webs W2 at positions substantially distant from each other on the continuous absorption body S, and it is necessary to arrange the cut webs W2 such that the pitches in the longitudinal direction of the continuous absorption body S are large in the manufacturing device according to the present invention as described later.

Next, the entire manufacturing device according to the present invention will be described with reference to FIGS. 1 and 2. The arrangement station SP in FIG. 2 is provided with a reception roll 43. The cut web W2 is arranged on the continuous absorption body S at the arrangement station SP in units of each wearing item.

In FIG. 1, the continuous web (an example of a continuous body) W that is not yet cut into the cut webs W2 is fed to the above-described drum 20 from a feeder 4. An absorption mechanism 5 is arranged at an upstream of the feeder 4, and a folding machine 6 is provided at a further upstream.

The folding machine 6 folds a whole cloth web that is a raw material of the continuous web W to generate the above-described continuous web W. The generated continuous web W is fed to the feeder 4 via the absorption mechanism 5 at the downstream.

The continuous web W is fed to the absorption mechanism 5 at a constant speed. The absorption mechanism 5 includes a dancer roll 52 that moves in a horizontal direction with respect to a base 51. The feeder 4 includes a belt 41 that conveys the continuous web W.

Next, the manufacturing device according to the present invention will be described in more detail.

As illustrated in FIG. 4, the drum 20 includes the preceding pad P1 that receives and holds the distal end part W1 of the continuous web W to convey, and the following pad P2 that catches up with the preceding pad and holds the distal end part W1 of the continuous web W together with the preceding pad. Both of the pads P1 and P2 approach the most closely at the cutting position CP. In this regard, the anvil Ai is arranged between both of the pads P1 and P2. Note that both of the pads P1 and P2 may not contact the anvil Ai.

The cutter 30 cuts the distal end part W1 of the continuous web W to generate the individual cut web W2 on the preceding pad P1. Note that an edge tip of the edge 31 of the cutter 30 may rotate at the same constant circumferential speed V as the circumferential speed of the anvils Ai.

The workpiece speed changer device 10 in FIG. 4 controls rotation of each pad such that relative speeds of both of the pads P1 and P2 are equal to each other and both of the pads P1 and P2 rotate at non constant speeds in at least part of a zone in a state where both of the preceding pads P1 and the following pad P2 hold the continuous web W. For example, both of the pads rotate at the constant speed V from a state immediately before cutting in FIG. 6A to a state at an instant of cutting in FIG. 6B. Meanwhile, while the preceding pad Pn may be accelerated and reach a speed (V+α) immediately after cutting in FIG. 5B, the following pad P2 may be decelerated and reach a speed (V−Δ).

Figure 5A:
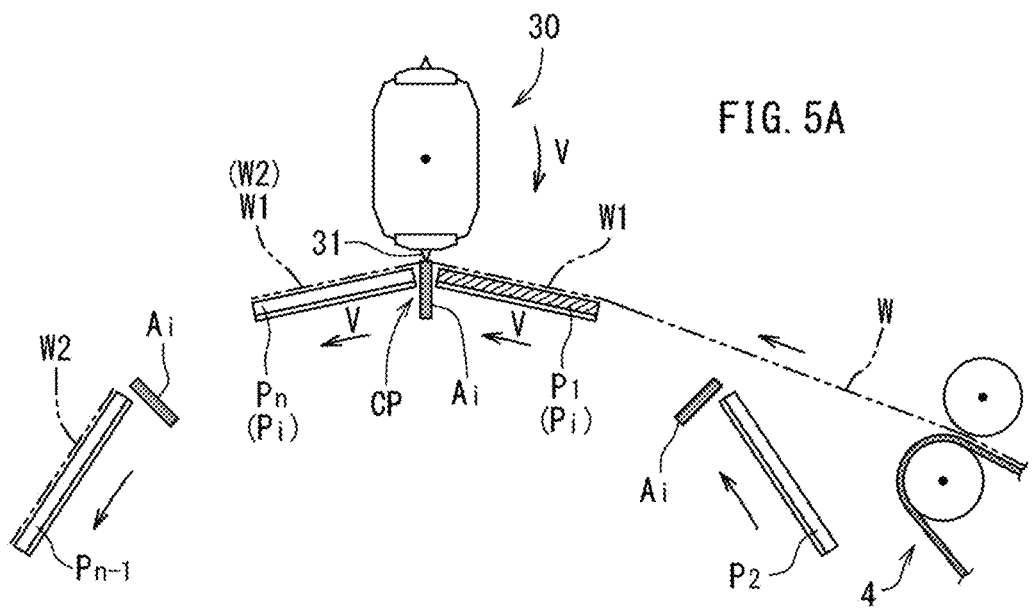
FIG. 5A is a schematic front view illustrating part of the drum in the cutting process from a final stage of a both holding process.
Figure 5B:
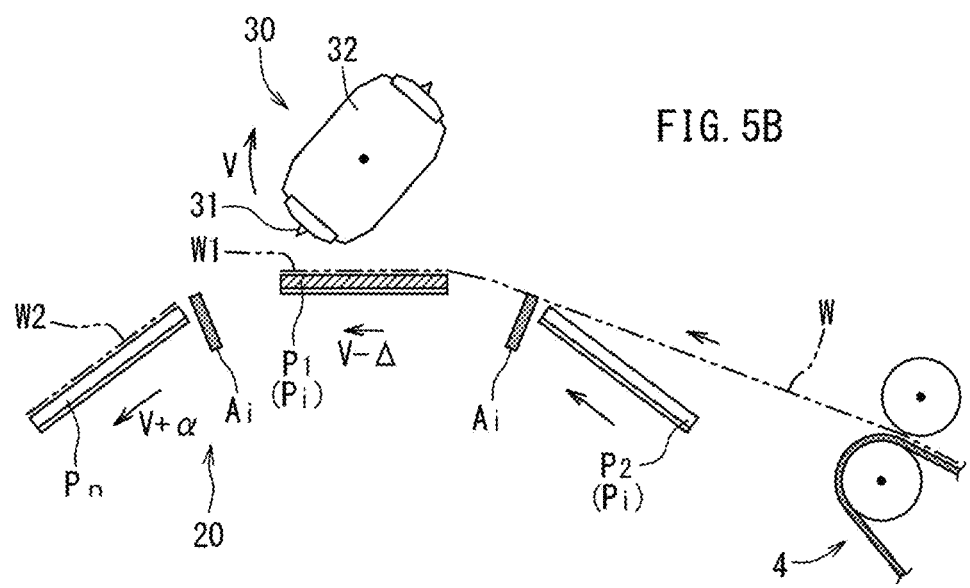
FIG. 5B is a schematic front view illustrating part of the drum in a state before the both holding process starts.
Figure 6A:
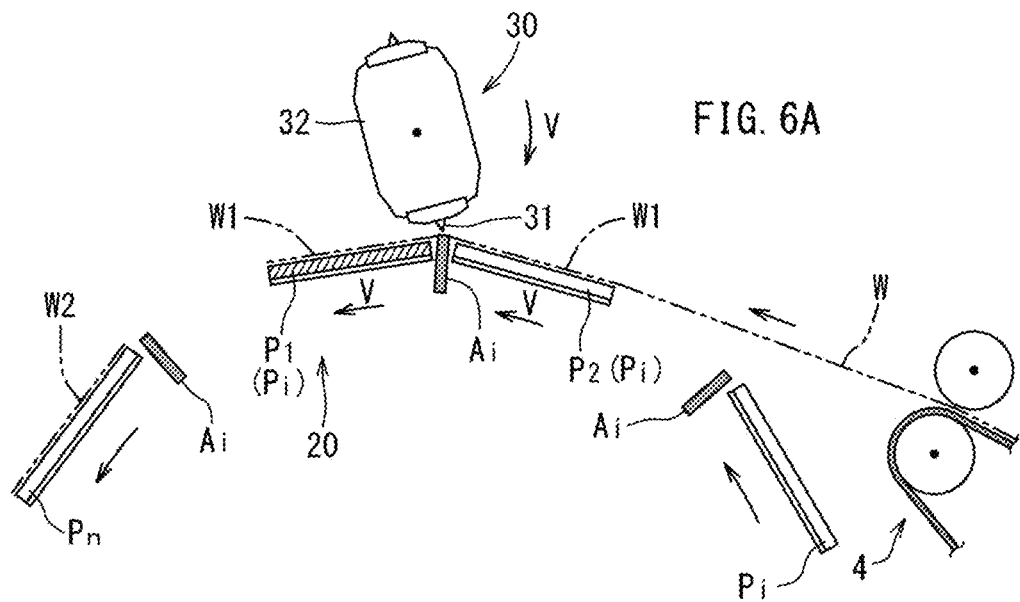
FIG. 6A is a schematic front view illustrating part of the drum in the both holding process immediately before the cutting process.

In FIGS. 5B and 6A, the distal end part W1 of the continuous web W is suctioned and held by the pad P1. Meanwhile, the pad P1 rotates at a non-constant speed from a state immediately after cutting in FIG. 5B to a state immediately before next cutting in FIG. 6A, and the continuous web W suctioned by the pad P1 is also conveyed at a non constant speed. In accordance with this conveyance, the feeder 4 (FIG. 3B) feeds the continuous web W to the drum 20 at a non-constant speed in response to a change in the speed of the pad P1 that rotates at the non constant speed.

The feeder 4 in FIG. 2 is configured as a belt conveyer that includes the belt 41 that suctions and conveys the continuous web W, and changes the feeding speed of the continuous web W by changing an operation speed of the belt 41. Note that a rotation speed of the belt 41 may be controlled by a servo motor.

The absorption mechanism 5 at the upstream of the belt conveyer in FIG. 1 absorbs the change in the feeding speed of the continuous web W in response to a change in the operation speed. The dancer roll 52 of the absorption mechanism 5 retains the continuous web W when swinging to the left and the right to decelerate the feeding speed, and lets out the retained continuous web W when increasing the feeding speed.

Next, acceleration and deceleration of each pad Pi will be described. As illustrated in FIG. 3B, each pad Pi is accelerated in an acceleration zone Tα, and is decelerated in a deceleration zone Tβ. Furthermore, each pad Pi moves at a constant low speed VMIN in a low speed zone TL, and moves at a constant maximum speed VMAX in a high speed zone TH.

That is, each pad Pi conveys the cut web W2 at the low speed VMIN in the low speed zone TL after passing the cutting position CP in FIG. 3B. Each pad Pi having passed through this low speed zone TL is accelerated to the maximum speed VMAX in the acceleration zone Tα as each pad Pi approaches the arrangement station SP. The speed of the preceding pad is higher than the speed of the following pad in this acceleration zone Tα, and the distance between the respective pads Pi expands.

Meanwhile, each pad Pi enters the high speed zone TH at the maximum speed VMAX, and arranges the cut web W2 on the continuous absorption body S while keeping the maximum speed VMAX. When passing through the high speed zone TH after arranging the cut web W2, each pad Pi travels toward the cutting position CP while decelerating in the deceleration zone Tβ. The speed of the following pad is higher than the speed of the preceding pad in this deceleration zone Tβ, and the distance between the respective pads Pi shortens.

Next, an outline of the manufacturing method will be briefly described. In FIG. 2, the continuous web W is fed from the feeder 4, and the distal end part of the continuous web W is held by the pad Pi of the drum 20. The continuous web W is cut at the anvils Ai of the drum 20 one after another to generate the cut webs W2.

When each pad Pi is accelerated in a workpiece speed change process in a state where each generated cut web W2 is held by the pad Pi, the distance between the respective cut webs W2 is expanded, and the posture of each pad Pi is turned 90° as illustrated in FIG. 3A until each pad Pi reaches the arrangement station SP. In this way, the cut webs W2 that are discontinuous in the convey direction are conveyed to the arrangement station SP. Each conveyed cut web W2 is arranged on the continuous absorption body S one after another at the arrangement station SP.

Note that a laminated body formed by intermittently arranging the cut webs W2 on the continuous absorption body S in FIG. 8 is generated as the individual wearing items N by cutting the continuous absorption body S along the virtual second cutting line C2 on the cut web W2 at an unillustrated manufacturing facility.

Next, details of feeding and cutting of the continuous web W in FIG. 1 will be described.

The workpiece conveying device 1, the feeder 4, and the dancer roll 52 repeatedly perform following operations.

In the state immediately before cutting in FIG. 5A to the state after previous cutting in FIG. 5B, the hatched preceding pad P1 receives the distal end part W1 of the continuous web W. While this preceding pad P1 continues decelerating after previous cutting, the following pad P2 also gradually catches up with the preceding pad P1 while decelerating. That is, although both of the pads P1 and P2 are decelerating, the circumferential speed of the following pad P2 is higher than that of the preceding pad P1 in the deceleration zone Tβ (FIG. 3B).

Figure 6B:
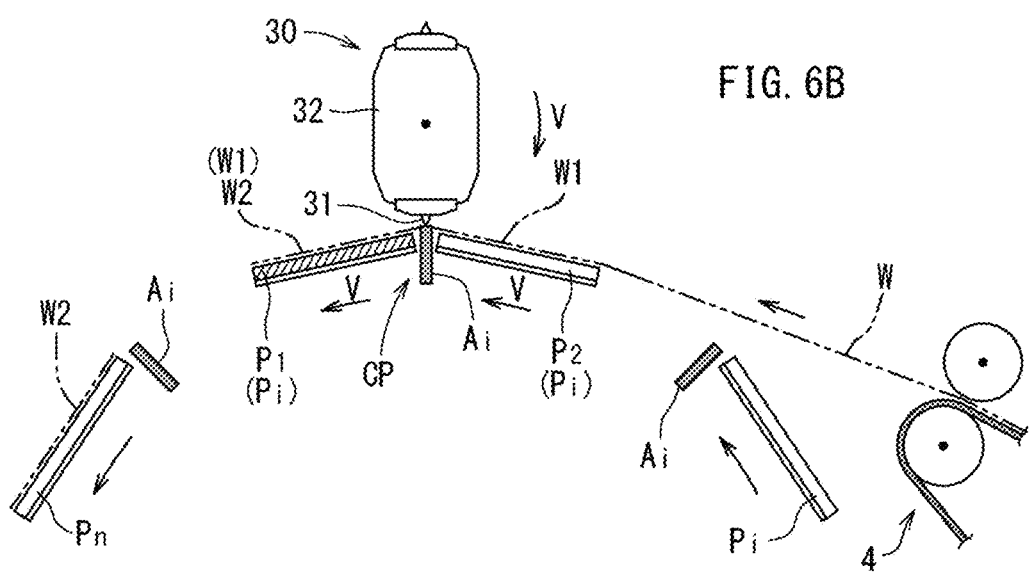
FIG. 6B is a schematic front view illustrating part of the drum in the cutting process.

Eventually, as illustrated in FIG. 6A, immediately before the continuous web W is cut, a both holding process where both of the preceding pad P1 and the following pad P2 hold the continuous web W starts. In this both holding process, the relative speeds of both of the pads P1 and P2 are equal, and the both holding process is executed in the low speed zone TL in FIG. 3B. When the anvil Ai reaches the cutting position CP in this state as illustrated in FIG. 6B, the distal end part W1 of the continuous web W is cut, and the individual cut web W2 is generated on the preceding pad P1.

Subsequently, after a cutting process where the preceding pad P1 has passed the cutting position CP, an acceleration process where the preceding pad P1 enters the acceleration zone Tα (FIG. 3B), and conveys the cut web W2 while being accelerated is executed.

As described above, after a pad Pi in FIG. 5A receives the continuous web W, a deceleration process where the corresponding pad Pi is decelerated in the deceleration zone Tβ in FIG. 3B is executed immediately after the cutting as shown in FIG. 5B until immediately before the cutting shown in FIG. 6A. Hence, the continuous web W fed from the feeder 4 to the workpiece conveying device 1 in FIG. 2 is also decelerated. The continuous web W is decelerated when the servo motor that drives and rotates the belt 41 in FIG. 2 is decelerated.

Meanwhile, the continuous web W to be introduced to the feeder 4 is also decelerated in response to deceleration of the fed continuous web W in FIG. 1. This deceleration is executed when the continuous web W is retained by the dancer roll 52. In a case of this example, when the dancer roll 52 in FIG. 1 moves in a retention direction D3 on the right side, the continuous web W is retained by the absorption mechanism 5.

When the dancer roll 52 moves in an unrolling (releasing) direction D4 opposite to the retention direction D3, the continuous web W retained by the absorption mechanism 5 is to be unrolled (let out) in response to an increase in the feeding speed of the continuous web W, and the releasing is to be accelerated. At this time, the speed of the belt 41 of the feeder 4 is to be increased. Meanwhile, the pad P1 to which the continuous web W has been fed is to increase the speed after the state shown in FIG. 5B.

Thus, both of the pads rotate at non-constant speeds in part of a zone in the both holding process in FIG. 6A, and the continuous web W is fed from the feeder 4 to the drum 20 at the non constant speeds in response to the change of the speeds of both of these pads. Consequently, it is possible to change the speed of the pad Pi at a point of time when the continuous web W starts being fed, and shorten the zone of the low speed zone TL of the constant speed in FIG. 3B. As a result, it is possible to increase the pitches between the neighboring cut webs W2 without increasing the diameter of the drum 20.

The above embodiment includes the following preferable invention.

According to a preferable manufacturing method, at an instant of cutting, the relative speeds of both of the pads are equal, and both of the pads rotate at a constant speed, and the preferable manufacturing method further includes an acceleration step where the preceding pad is accelerated after the cutting.

According to another preferable manufacturing method, at an instant of cutting, the relative speeds of both of the pads are equal, and both of the pads rotate at a constant speed, and another preferable manufacturing method further includes a deceleration step where the following pad is decelerated after the cutting.

In these cases, it is difficult for an unintended tension to act on the continuous body at the time of cutting. Consequently, it is difficult for variation to occur in the quality of workpieces.

In a preferable manufacturing device, the feeder is configured as a belt conveyer that includes a belt that suctions and conveys the continuous body, and changes a feeding speed of the continuous body by changing an operation speed of the belt.

In this case, it is difficult for the continuous body to be fed to the drum to unintentionally become relaxed or tense.

A further preferable manufacturing device includes at an upstream of the belt conveyer an absorption mechanism that absorbs the change of the feeding speed of the continuous body in response to the change in the operation speed.

In this case, the feeder can easily change the speed of and feed the continuous body.

In the further preferable manufacturing device, the absorption mechanism includes a dancer roll that retains the continuous body when decreasing the feeding speed, and lets out the retained continuous body when increasing the feeding speed.

In this case, it is possible to easily absorb the change in the feeding speed of the continuous body.

Features described and/or illustrated in association with one embodiment or each preferable embodiment can be used in the same or similar way as or to one or more other embodiments and/or in combination with or instead of the other embodiments.

As described above, although the preferred embodiment has been described with reference to the drawings, one of ordinary skill in the art can easily assume various changes and corrections within an obvious range in view of this description.

For example, the pads may not turn about the normal line.

Furthermore, the pads and the anvils do not need to be separate bodies, and the anvils may be integrally provided at downstream ends or upstream ends of the pads.

Consequently, it is interpreted that such changes and corrections are within the scope of the present invention defined based on the claims.

INDUSTRIAL APPLICABILITY

The present invention can be used for a disposable wearing item, and a manufacturing method therefor.

REFERENCE SIGNS LIST

1: Workpiece conveying device
10: Workpiece speed changer device
11: First arm
12: Second arm
13: Pad frame
20: Drum
21: Guiding means
30: Cutter
32: Cutter roll
31: Edge
4: Feeder
41: Belt
43: Reception roll
5: Absorption mechanism
51: Base
52: Dancer roll
6: Folding machine
Ai: Anvil
C1: First cutting line
C2: Second cutting line
D1: First direction
D2: Second direction
D3: Retention direction
D4: Unrolling direction
Pi: Pad
r: Normal line
N: Wearing item (absorptive item)
S: Continuous absorption body
S3: Absorptive body
Tα: Acceleration section
Tβ: Deceleration section
TH: High speed zone
TL: Low speed zone
X1: First axial line
X2: Second axial line
CP: Cutting position
RP: Reception position
SP: Arrangement station
W: Continuous web (example of continuous body)
W1: Distal end part
W2: Cutting web (example of workpiece)
Wα: Bonding area
Wf: Rubber thread
Wp: Pocket member

The invention claimed is:

1. A manufacturing method for a wearing item for feeding a continuous body from a feeder to a drum including a plurality of pads that rotate with a circumferential speed being changed, cutting a distal end part of the continuous body one after another to generate individual workpieces on the pads one after another, and passing the workpieces to a downstream process in a state where a distance between the pads that hold the workpieces is expanded, and an interval between neighboring workpieces of the workpieces is increased, the manufacturing method for the wearing item comprising:
a step of, at a preceding pad, receiving and holding the distal end part of the continuous body to convey;
a step of, at a following pad, catching up with the preceding pad;
a both holding step of, at both of the preceding pad and the following pad, holding the continuous body; and
a cutting step of cutting the distal end part of the continuous body to generate an individual workpiece on the preceding pad, wherein
the manufacturing method repeatedly executes the receiving and holding step, the catching up step, the both holding step, and the cutting step,
in the both holding step, relative speeds of both of the preceding and following pads are equal to each other, and both of the preceding and following pads rotate at a non constant speed in at least part of a zone, and
the continuous body is fed from the feeder at the non-constant speed in response to a change in a speed of the preceding and following pads that rotate at the non constant speed.

2. The manufacturing method for the wearing item according to claim 1, wherein
at an instant of the cutting, the relative speeds of both of the pads are equal, and both of the pads rotate at a constant speed, and the manufacturing method for the wearing item further comprises an acceleration step where the preceding pad is accelerated after the cutting.

3. The manufacturing method for the wearing item according to claim 1, wherein
at an instant of the cutting, the relative speeds of both of the pads are equal, and both of the pads rotate at a constant speed, and
the manufacturing method for the wearing item further comprises a deceleration step where the following pad is decelerated after the cutting.

4. A manufacturing device for a wearing item that feeds a continuous body to a drum including a plurality of pads that rotate with a circumferential speed being changed, cuts a distal end part of the continuous body one after another to generate individual workpieces on the pads one after another, and passes the workpieces to a downstream process in a state where a distance between the pads that hold the workpieces is expanded, and an interval between neighboring workpieces of the workpieces is increased, the manufacturing device for the wearing item comprising:
a preceding pad that receives and holds the distal end part of the continuous body to convey;
a following pad that catches up with the preceding pad and holds the continuous body together with the preceding pad;
a cutter that cuts the distal end part of the continuous body to generate an individual workpiece on the preceding pad;
a workpiece speed changer device that controls rotation of the preceding pad and the following pad in a state where both of the preceding pad and the following pad hold the continuous body such that relative speeds of both of the preceding and following pads are equal to each other, and both of the preceding and following pads rotate at a non constant speed in at least part of a zone; and
a feeder that feeds the continuous body to the drum at the non constant speed in response to a change in a speed of the preceding and following pads that rotate at the non-constant speed.

5. The manufacturing device for the wearing item according to claim 4, wherein the feeder is configured as a belt conveyer that includes a belt that suctions and conveys the continuous body, and changes a feeding speed of the continuous body by changing an operation speed of the belt.

6. The manufacturing device for the wearing item according to claim 5, further comprising at an upstream of the belt conveyer an absorption mechanism that absorbs the change of the feeding speed of the continuous body in response to the change in the operation speed.

7. The manufacturing device for the wearing item according to claim 6, wherein the absorption mechanism includes a dancer roll that retains the continuous body when decreasing the feeding speed, and lets out the retained continuous body when increasing the feeding speed.

* * * * *